(12) United States Patent
George (10) Patent No.: US 11,439,430 B2
(45) Date of Patent: Sep. 13, 2022

(54) SURGICAL ACCESS DEVICE WITH AIR RELEASE MECHANISM

(71) Applicant: Covidien LP, Mansfield, MA (US)

(72) Inventor: Sabastian K. George, Hyderabad (IN)

(73) Assignee: Covidien LP, Mansfield, MA (US)

( * ) Notice: Subject to any disclaimer, the term of this patent is extended or adjusted under 35 U.S.C. 154(b) by 171 days.

(21) Appl. No.: 16/871,723

(22) Filed: May 11, 2020

(65) Prior Publication Data

US 2021/0346056 A1 Nov. 11, 2021

(51) Int. Cl.
*A61B 17/34* (2006.01)

(52) U.S. Cl.
CPC ...... *A61B 17/3423* (2013.01); *A61B 17/3496* (2013.01); *A61B 17/3498* (2013.01); *A61B 2017/3486* (2013.01)

(58) Field of Classification Search
CPC ......... A61B 17/3423; A61B 2017/3425–3427; A61B 17/3496; A61B 17/3498; A61B 2017/3486; A61B 2017/3492; A61B 2017/348–3484; A61B 17/0218; A61B 17/3421; A61M 25/1018; A61M 25/10–2025/1097

See application file for complete search history.

(56) References Cited

U.S. PATENT DOCUMENTS

| 397,060 A | 1/1889 | Knapp |
| 512,456 A | 1/1894 | Sadikova |
| 1,213,005 A | 1/1917 | Pillsbury |
| 2,912,981 A | 11/1959 | Keough |
| 2,936,760 A | 5/1960 | Gains |
| 3,039,468 A | 6/1962 | Price |
| 3,050,066 A | 8/1962 | Koehn |
| 3,253,594 A | 5/1966 | Matthews et al. |
| 3,397,699 A | 8/1968 | Kohl |

(Continued)

FOREIGN PATENT DOCUMENTS

| EP | 0480653 A1 | 4/1992 |
| EP | 0610099 A2 | 8/1994 |

(Continued)

OTHER PUBLICATIONS

Extended European Search Report dated Sep. 21, 2021 issued in corresponding EP Appln. No 21173013.0.

*Primary Examiner* — Diane D Yabut
*Assistant Examiner* — Brigid K Byrd
(74) *Attorney, Agent, or Firm* — Carter, Deluca & Farrell LLP (57) ABSTRACT

A surgical access device includes an elongate tubular member with a proximal region and a distal region. A passage extends through the elongate tubular member. The surgical access device also includes a balloon anchor with an expandable portion. A first portion of the balloon anchor extends proximally along the outer surface of the tubular member. The surgical access device also has a valve assembly disposed in the proximal region of the elongate tubular member that is fluidly coupled to the balloon anchor. A disc is slidably disposed on the elongate tubular member and includes a first blade with a first sharpened edge that is configured to penetrate the first portion of the balloon anchor. The first blade is transitionable between a retracted position and an extended position.

7 Claims, 8 Drawing Sheets

(56) References Cited

U.S. PATENT DOCUMENTS

| | | | |
|---|---|---|---|
| 3,545,443 A | 12/1970 | Ansari et al. | |
| 3,713,447 A | 1/1973 | Adair | |
| 3,774,596 A | 11/1973 | Cook | |
| 3,800,788 A | 4/1974 | White | |
| 3,882,852 A | 5/1975 | Sinnreich | |
| 3,896,816 A | 7/1975 | Mattler | |
| 3,961,632 A | 6/1976 | Moossun | |
| 3,985,139 A * | 10/1976 | Penar | A61M 25/10 604/99.01 |
| RE29,207 E | 5/1977 | Bolduc et al. | |
| 4,083,369 A | 4/1978 | Sinnreich | |
| 4,217,889 A | 8/1980 | Radovan et al. | |
| 4,243,050 A | 1/1981 | Littleford | |
| 4,276,874 A | 7/1981 | Wolvek et al. | |
| 4,312,353 A | 1/1982 | Shahbabian | |
| 4,327,709 A | 5/1982 | Hanson et al. | |
| 4,345,606 A | 8/1982 | Littleford | |
| 4,411,654 A | 10/1983 | Boarini et al. | |
| 4,416,267 A | 11/1983 | Garren et al. | |
| 4,490,137 A | 12/1984 | Moukheibir | |
| 4,496,345 A | 1/1985 | Hasson | |
| 4,574,806 A | 3/1986 | McCarthy | |
| 4,581,025 A | 4/1986 | Timmermans | |
| 4,596,554 A | 6/1986 | Dastgeer | |
| 4,596,559 A | 6/1986 | Fleischhacker | |
| 4,608,965 A | 9/1986 | Anspach, Jr. et al. | |
| 4,644,936 A | 2/1987 | Schiff | |
| 4,654,030 A | 3/1987 | Moll et al. | |
| 4,685,447 A | 8/1987 | Iversen et al. | |
| 4,701,163 A | 10/1987 | Parks | |
| 4,738,666 A | 4/1988 | Fuqua | |
| 4,769,038 A | 9/1988 | Bendavid et al. | |
| 4,772,266 A | 9/1988 | Groshong | |
| 4,779,611 A | 10/1988 | Grooters et al. | |
| 4,784,133 A | 11/1988 | Mackin | |
| 4,793,348 A | 12/1988 | Palmaz | |
| 4,798,205 A | 1/1989 | Bonomo et al. | |
| 4,800,901 A | 1/1989 | Rosenberg | |
| 4,802,479 A | 2/1989 | Haber et al. | |
| 4,813,429 A | 3/1989 | Eshel et al. | |
| 4,840,613 A | 6/1989 | Balbierz | |
| 4,854,316 A | 8/1989 | Davis | |
| 4,861,334 A | 8/1989 | Nawaz | |
| 4,865,593 A | 9/1989 | Ogawa et al. | |
| 4,869,717 A | 9/1989 | Adair | |
| 4,888,000 A | 12/1989 | McQuilkin et al. | |
| 4,899,747 A | 2/1990 | Garren et al. | |
| 4,917,668 A | 4/1990 | Haindl | |
| 4,931,042 A | 6/1990 | Holmes et al. | |
| 4,955,895 A | 9/1990 | Sugiyama et al. | |
| 5,002,557 A | 3/1991 | Hasson | |
| 5,009,643 A | 4/1991 | Reich et al. | |
| 5,030,206 A | 7/1991 | Lander | |
| 5,030,227 A | 7/1991 | Rosenbluth et al. | |
| 5,074,871 A | 12/1991 | Groshong | |
| 5,098,392 A | 3/1992 | Fleischhacker et al. | |
| 5,104,383 A | 4/1992 | Shichman | |
| 5,116,318 A | 5/1992 | Hillstead | |
| 5,116,357 A | 5/1992 | Eberbach | |
| 5,122,122 A | 6/1992 | Allgood | |
| 5,122,155 A | 6/1992 | Eberbach | |
| 5,137,512 A | 8/1992 | Burns et al. | |
| 5,141,494 A | 8/1992 | Danforth et al. | |
| 5,141,515 A | 8/1992 | Eberbach | |
| 5,147,302 A | 9/1992 | Euteneuer et al. | |
| 5,147,316 A | 9/1992 | Castillenti | |
| 5,147,374 A | 9/1992 | Fernandez | |
| 5,158,545 A | 10/1992 | Trudell et al. | |
| 5,159,925 A | 11/1992 | Neuwirth et al. | |
| 5,163,949 A | 11/1992 | Bonutti | |
| 5,176,692 A | 1/1993 | Wilk et al. | |
| 5,176,697 A | 1/1993 | Hasson et al. | |
| 5,183,463 A | 2/1993 | Debbas | |
| 5,188,596 A | 2/1993 | Condon et al. | |
| 5,188,630 A | 2/1993 | Christoudias | |
| 5,195,507 A | 3/1993 | Bilweis | |
| 5,201,742 A | 4/1993 | Hasson | |
| 5,201,754 A | 4/1993 | Crittenden et al. | |
| 5,209,725 A | 5/1993 | Roth | |
| 5,215,526 A | 6/1993 | Deniega et al. | |
| 5,222,970 A | 6/1993 | Reeves | |
| 5,226,890 A | 7/1993 | Ianniruberto et al. | |
| 5,232,446 A | 8/1993 | Arney | |
| 5,232,451 A | 8/1993 | Freitas et al. | |
| 5,234,454 A | 8/1993 | Bangs | |
| 5,250,025 A | 10/1993 | Sosnowski et al. | |
| 5,258,026 A | 11/1993 | Johnson et al. | |
| 5,269,753 A | 12/1993 | Wilk | |
| 5,290,249 A | 3/1994 | Foster et al. | |
| 5,308,327 A | 5/1994 | Heaven et al. | |
| 5,309,896 A | 5/1994 | Moll et al. | |
| 5,314,443 A | 5/1994 | Rudnick | |
| 5,318,012 A | 6/1994 | Wilk | |
| 5,330,497 A | 7/1994 | Freitas et al. | |
| 5,342,307 A | 8/1994 | Euteneuer et al. | |
| 5,346,504 A | 9/1994 | Ortiz et al. | |
| 5,359,995 A | 11/1994 | Sewell, Jr. | |
| 5,361,752 A | 11/1994 | Moll et al. | |
| 5,370,134 A | 12/1994 | Chin et al. | |
| 5,383,889 A | 1/1995 | Warner et al. | |
| 5,397,311 A | 3/1995 | Walker et al. | |
| 5,402,772 A | 4/1995 | Moll et al. | |
| 5,407,433 A | 4/1995 | Loomas | |
| 5,431,173 A | 7/1995 | Chin et al. | |
| 5,445,615 A | 8/1995 | Yoon | |
| 5,468,248 A | 11/1995 | Chin et al. | |
| 5,514,091 A | 5/1996 | Yoon | |
| 5,514,153 A | 5/1996 | Bonutti | |
| 5,540,658 A | 7/1996 | Evans et al. | |
| 5,540,711 A | 7/1996 | Kieturakis et al. | |
| 5,607,441 A | 3/1997 | Sierocuk et al. | |
| 5,607,443 A | 3/1997 | Kieturakis et al. | |
| 5,632,761 A * | 5/1997 | Smith | A61B 1/00082 600/207 |
| 5,656,013 A | 8/1997 | Yoon | |
| 5,667,479 A | 9/1997 | Kieturakis | |
| 5,667,520 A | 9/1997 | Bonutti | |
| 5,704,372 A | 1/1998 | Moll et al. | |
| 5,707,382 A | 1/1998 | Sierocuk et al. | |
| 5,713,869 A | 2/1998 | Morejon | |
| 5,722,986 A | 3/1998 | Smith et al. | |
| 5,728,119 A | 3/1998 | Smith et al. | |
| 5,730,748 A | 3/1998 | Fogarty et al. | |
| 5,730,756 A | 3/1998 | Kieturakis et al. | |
| 5,738,628 A | 4/1998 | Sierocuk et al. | |
| 5,755,693 A | 5/1998 | Walker et al. | |
| 5,762,604 A | 6/1998 | Kieturakis | |
| 5,772,680 A | 6/1998 | Kieturakis et al. | |
| 5,779,728 A | 7/1998 | Lunsford et al. | |
| 5,797,947 A | 8/1998 | Mollenauer | |
| 5,803,901 A | 9/1998 | Chin et al. | |
| 5,810,867 A | 9/1998 | Zarbatany et al. | |
| 5,814,060 A | 9/1998 | Fogarty et al. | |
| 5,836,913 A | 11/1998 | Orth et al. | |
| 5,836,961 A | 11/1998 | Kieturakis et al. | |
| 5,865,802 A | 2/1999 | Yoon et al. | |
| 5,893,866 A | 4/1999 | Hermann et al. | |
| 5,925,058 A | 7/1999 | Smith et al. | |
| 6,361,543 B1 | 3/2002 | Chin et al. | |
| 6,368,337 B1 | 4/2002 | Kieturakis et al. | |
| 6,375,665 B1 | 4/2002 | Nash et al. | |
| 6,379,372 B1 | 4/2002 | Dehdashtian et al. | |
| 6,432,121 B1 | 8/2002 | Jervis | |
| 6,447,529 B2 | 9/2002 | Fogarty et al. | |
| 6,468,205 B1 | 10/2002 | Mollenauer et al. | |
| 6,506,200 B1 | 1/2003 | Chin | |
| 6,514,272 B1 | 2/2003 | Kieturakis et al. | |
| 6,517,514 B1 | 2/2003 | Campbell | |
| 6,527,787 B1 | 3/2003 | Fogarty et al. | |
| 6,540,764 B1 | 4/2003 | Kieturakis et al. | |
| 6,796,960 B2 | 9/2004 | Cioanta et al. | |
| 8,454,645 B2 | 6/2013 | Criscuolo et al. | |

(56) References Cited

U.S. PATENT DOCUMENTS

| | | | |
|---|---|---|---|
| 2009/0264913 A1* | 10/2009 | Hart | A61M 25/1002 |
| | | | 606/185 |
| 2014/0277059 A1* | 9/2014 | Lam | A61B 17/24 |
| | | | 606/192 |
| 2020/0107859 A1 | 4/2020 | Zhu | |

FOREIGN PATENT DOCUMENTS

| | | |
|---|---|---|
| EP | 0880939 A1 | 12/1998 |
| EP | 2589349 A1 | 5/2013 |
| EP | 3378422 A2 | 9/2018 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |

* cited by examiner

SURGICAL ACCESS DEVICE WITH AIR RELEASE MECHANISM

FIELD

The present disclosure relates to a surgical access device. More particularly, the present disclosure relates to a surgical access device having an air release mechanism.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula or an access port) is introduced through an opening in tissue (e.g., a naturally occurring orifice or an incision) to provide access to an underlying surgical site in the body. The opening is typically made using an obturator having a blunt or sharp tip that may be inserted through a passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instruments through the surgical access device to perform the surgical procedure.

Minimally invasive surgical procedures, including both endoscopic and laparoscopic procedures, permit surgery to be performed on organs, tissues, and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula accessing the abdominal cavity to perform one or more surgical tasks. The cannula may incorporate a seal to establish a substantially fluid tight seal about the laparoscopic instrument to preserve the integrity of the pneumoperitoneum. The cannula, which is subjected to the pressurized environment, e.g., the pneumoperitoneum, may include an anchor mechanism to prevent the cannula from backing out of the opening in the abdominal wall, for example, during manipulation of the laparoscopic instrument within the cannula or withdrawal of the laparoscopic instrument therefrom.

SUMMARY

The present disclosure relates to a surgical access device. The surgical access device includes an elongate tubular member having proximal and distal regions, the elongate tubular member defining a passage therethrough. A balloon anchor is disposed in the distal region of the elongate tubular member, the balloon anchor including an expandable portion. A first portion of the balloon anchor extends proximally along an outer surface of the elongate tubular member. A valve assembly is disposed in the proximal region of the elongate tubular member, the valve assembly fluidly coupled to the balloon anchor. A disc is slidably disposed on the elongate tubular member. A first blade having a first sharpened edge is slidably disposed in the disc and transitionable between a retracted position and an extended position, the first sharpened edge configured to penetrate the first portion of the balloon anchor.

In aspects, the surgical access device may include a valve housing disposed in the proximal region of the elongate tubular member.

In an aspect, the expandable portion of the balloon anchor may be transitionable between a collapsed configuration and an expanded configuration.

In an aspect, penetrating the first portion of the balloon anchor with the first blade transitions the expandable portion of the balloon anchor from the expanded configuration to the collapsed configuration.

In another aspect, the disc may include a second blade transitionable between a retracted position and an extended position, the second blade having a second sharpened edge.

In an aspect, translation of the first and second blades from the retracted positions to the extended positions may penetrate the first portion of the balloon anchor.

The present disclosure also relates to a method of removing a surgical access device from a surgical site. The method includes: sliding a disc distally along an elongate tubular member of a surgical access device; moving a blade of the disc towards an outer surface of the surgical access device; penetrating a first portion of a balloon anchor with a sharpened edge of the blade such that pressure within the balloon anchor equalizes with ambient pressure; and removing the surgical access device from the surgical site.

In aspects, penetrating the first portion of the balloon anchor may include rotating the disc with the sharpened edge of the blade engaged with the first portion of the expandable balloon.

Other features of the disclosure will be appreciated from the following description.

DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Aspects of the disclosure are described hereinbelow with reference to the accompanying drawings; however, it is to be understood that the disclosed devices are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Descriptions of technical features of an illustrative access device in accordance with the disclosure should typically be considered as available and applicable to other similar features of another device of the disclosure. Accordingly, technical features described herein in connection with one illustrative access device may be applicable to other devices of the disclosure, and thus duplicative descriptions may be omitted herein.

Aspects of the disclosure will be described more fully below (e.g., with reference to the accompanying drawings). Like reference numerals may refer to like elements throughout the specification and drawings.

Many access assemblies include an anchor mechanism for preventing withdrawal of the access assembly. These anchor mechanisms may be in the form of an inflatable balloon. Alternatively, the access assemblies may be maintained in position with an expandable flange or other structure capable of being collapsed to facilitate insertion of the access assembly through the tissue and selectively expanded to prevent withdrawal of the access assembly from the tissue.

Figure 1:
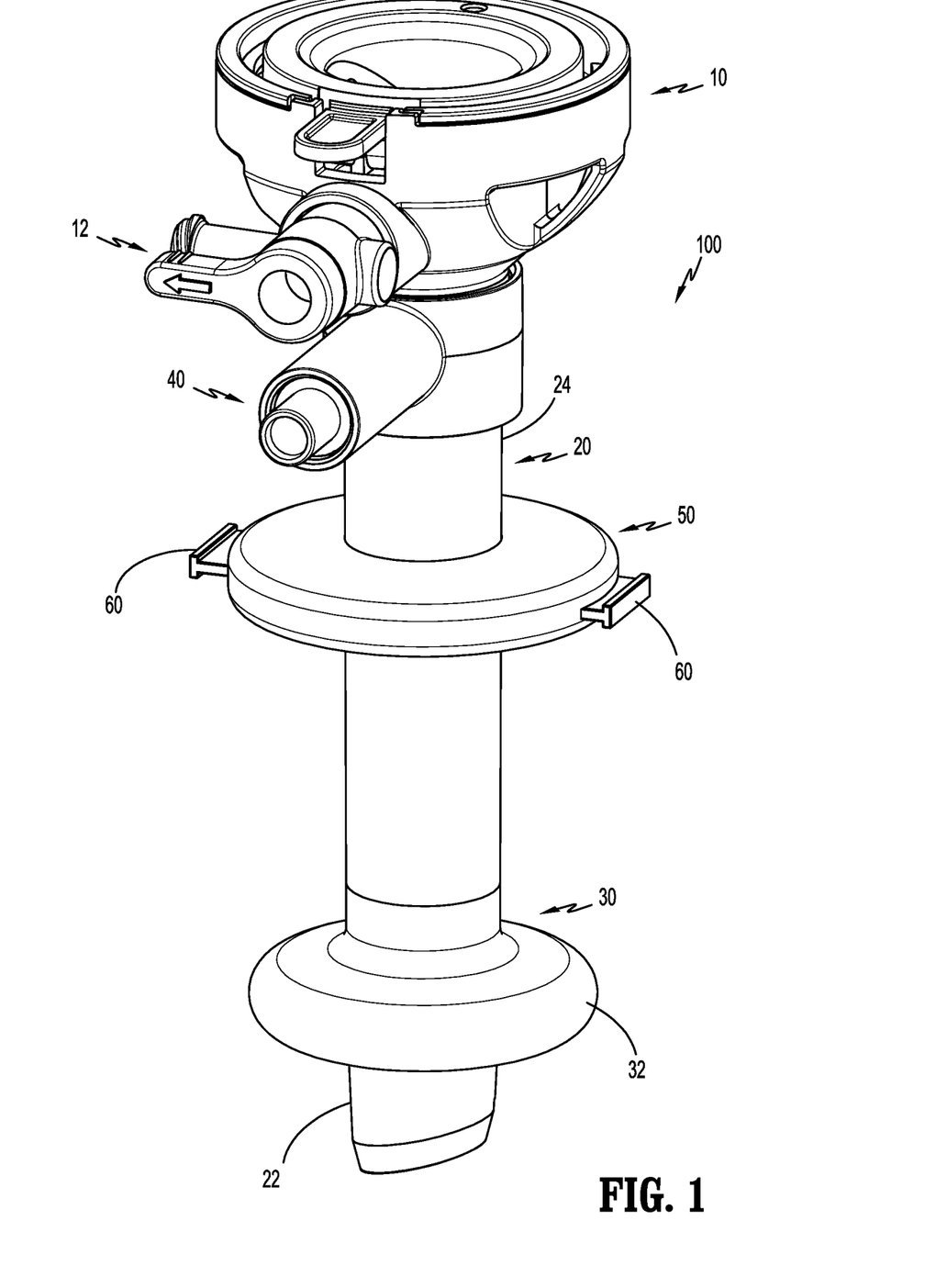
FIG. 1 is a perspective view of a surgical access device according to an aspect of the present disclosure.
Figure 2:
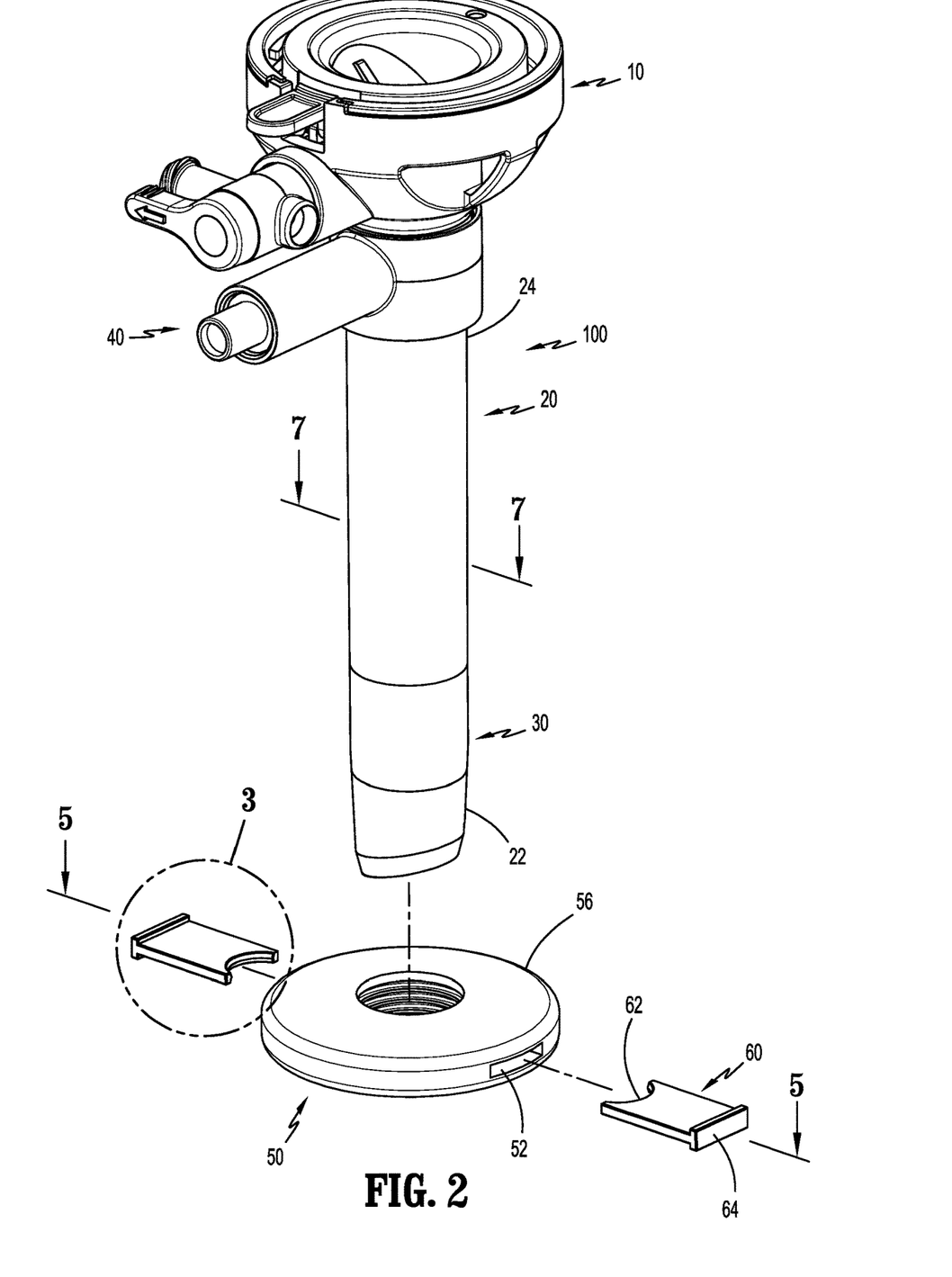
FIG. 2 is an exploded perspective view, with parts separated, of the surgical access device of FIG. 1.
Figure 7:
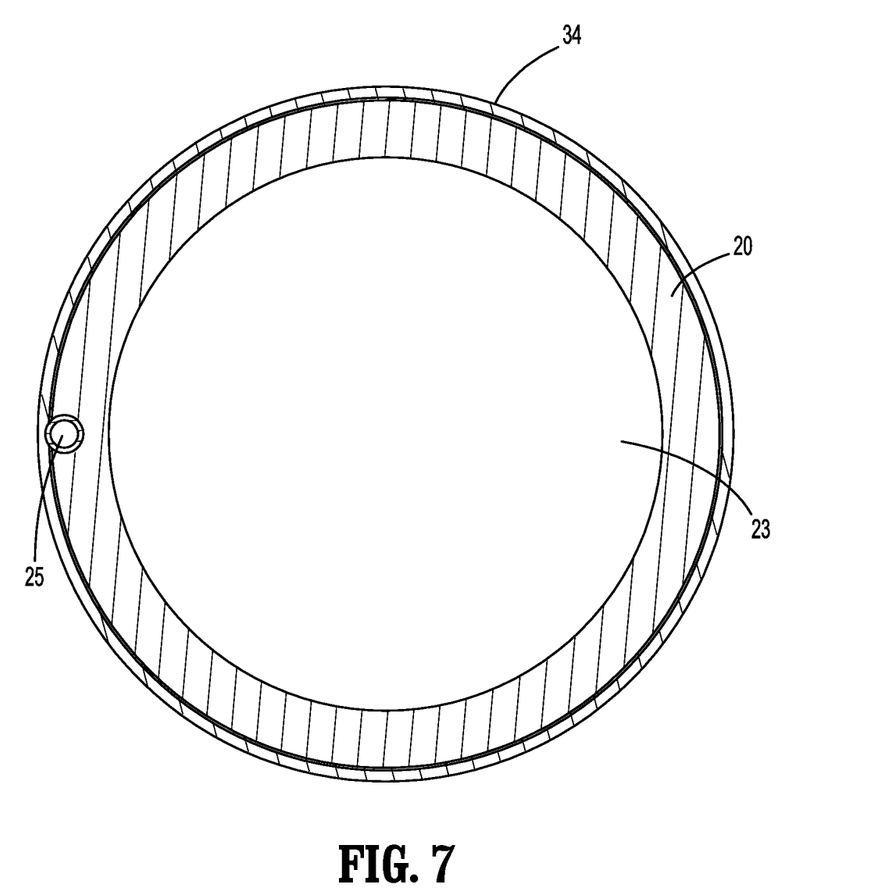
FIG. 7 is a top cross-sectional view of a cannula tube of the surgical access device of FIG. 1 and a proximal portion of the balloon anchor taken along section line 7-7 of FIG. 2.

With initial reference to FIGS. 1 and 2, a surgical access device 100 is illustrated. The surgical access device 100 has a housing assembly 10 with an elongated tubular member or cannula tube 20 extending distally therefrom. A balloon anchor 30 is attached to the cannula tube 20 with an expandable portion 32 disposed in a distal region 22 of the cannula tube 20 and a proximal portion 34a of the balloon anchor 30 that extends proximally along an outer surface of the cannula tube 20. A valve assembly 40 is coupled to a proximal region 24 of the cannula tube 20 adjacent to the housing assembly 10 and is in fluid communication with the balloon anchor 30 for expanding and/or collapsing the expandable portion 32 of the balloon anchor 30. The housing assembly 10 includes a valve 12 for introducing an insufflation fluid to a channel 23 of the cannula tube. Examples of suitable housings and valve assemblies are disclosed in U.S. patent application Ser. No. 16/800,566 filed on Feb. 25, 2020 and U.S. Pat. No. 10,588,662. With brief reference to FIG. 7, an inflation lumen 25 extends through the cannula tube 20 and provides fluid communication between the expandable portion 32 of the balloon anchor 30 and the valve assembly 40. A disc 50 is slidably disposed on an outer surface of the cannula tube 20 and is transitionable between a first or proximal position on the cannula tube 20 (FIG. 1) and a second or distal position (FIG. 8) on the cannula tube 20. In the proximal position, the disc 50 is proximate the valve assembly 40 and in the distal position, the disc 50 is proximate the expandable portion 32 of the balloon anchor 30. The disc 50 has diametrically opposed slots 52 that slidably receive first and second blades 60.

Figure 3:
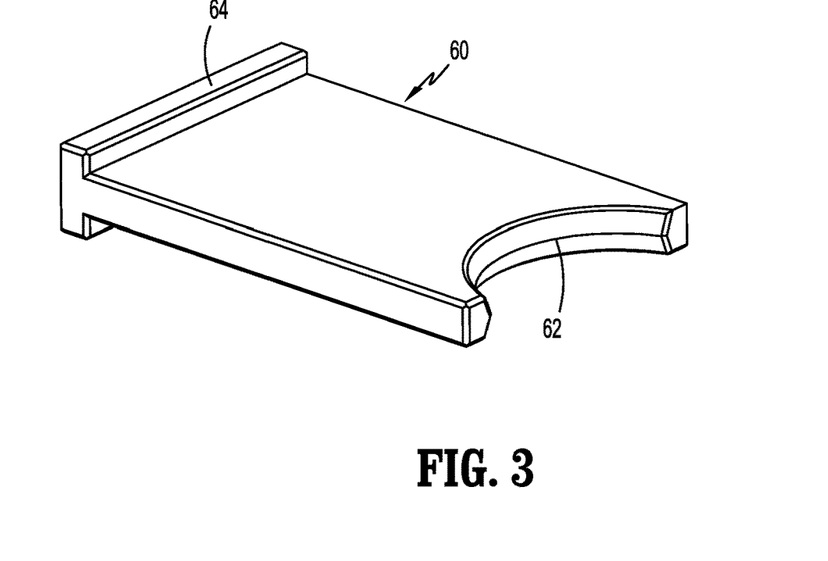
FIG. 3 is an enlarged view of the area of detail identified in FIG. 2.
Figure 5:
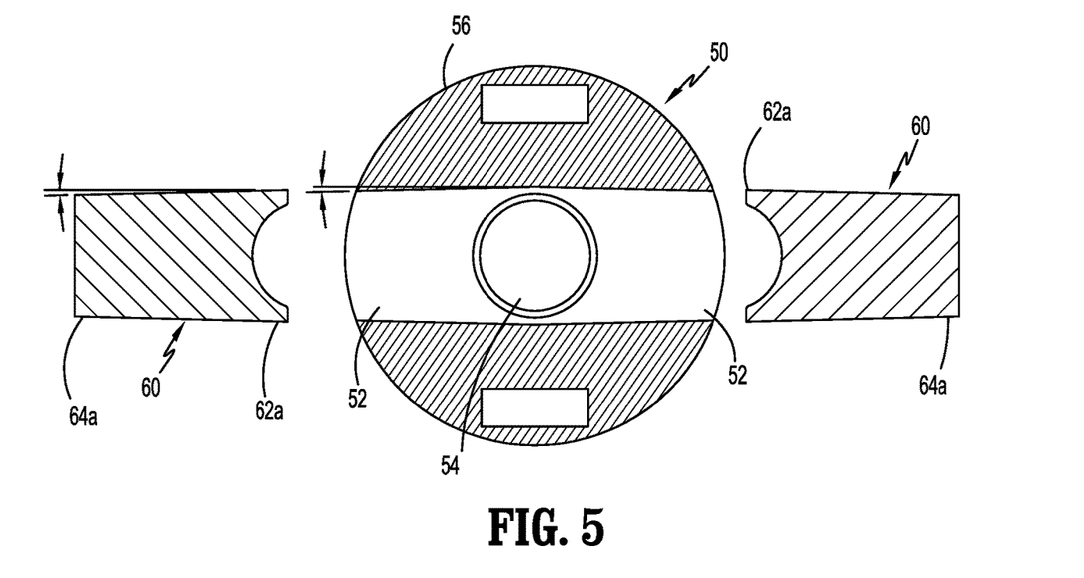
FIG. 5 is a top cross-sectional view of a disc and blades taken along section line 5-5 of FIG. 2.
Figure 6:
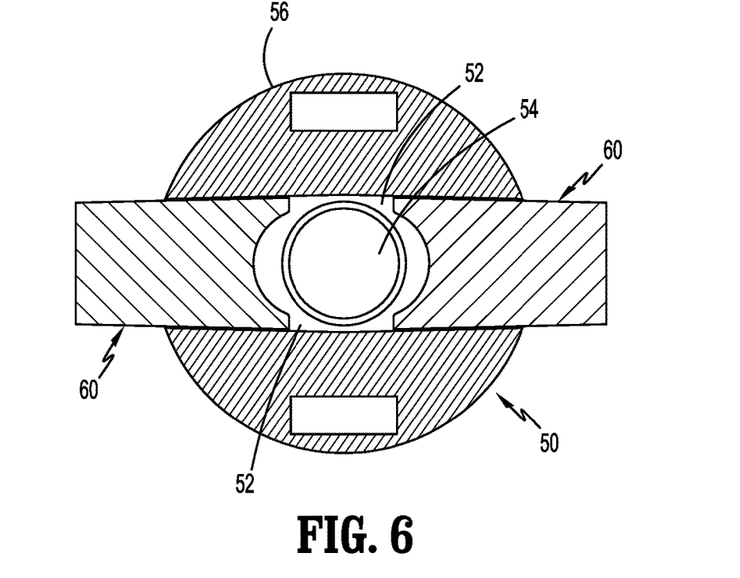
FIG. 6 is a top cross-sectional view of FIG. 5 with the blades in an extended position.

With additional reference to FIG. 3, each blade 60 has a sharpened distal end 62 and a rectangular grip 64 for facilitating actuation by a clinician. The distal end 62 has an arcuate profile complementary to the profile of the outer surface of the cannula tube 20. The sharpened distal end or knife edge 62 is located along the arcuate profile. Although illustrated with two blades 60, it is contemplated that a single blade 60 may be used or alternatively more than two blades 60 may be used. As shown in FIGS. 5 and 6, the disc 50 has diametrically opposed first and second slots 52 that slidably receive corresponding first and second blades 60 therein. The slots 52 vary in width (i.e., are tapered) between a maximum value proximate a central opening 54 of the disc 50 and a minimum value proximate an outer edge 56 of the disc 50. Likewise, each blade 60 is tapered with a maximum width at a distal end 62a and a minimum width at a proximal end 64a. By tapering the blades 60 and the slots 52 in this manner, each blade 60 resists removal from the disc 50 while allowing full insertion of the blades 60.

Figure 4:
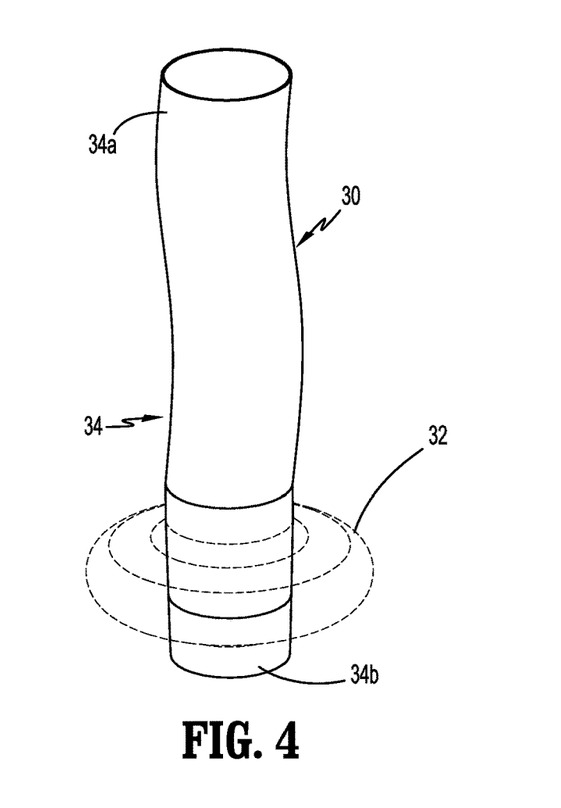
FIG. 4 is a perspective view of a balloon anchor of the surgical access device of FIG. 1.
Figure 8:
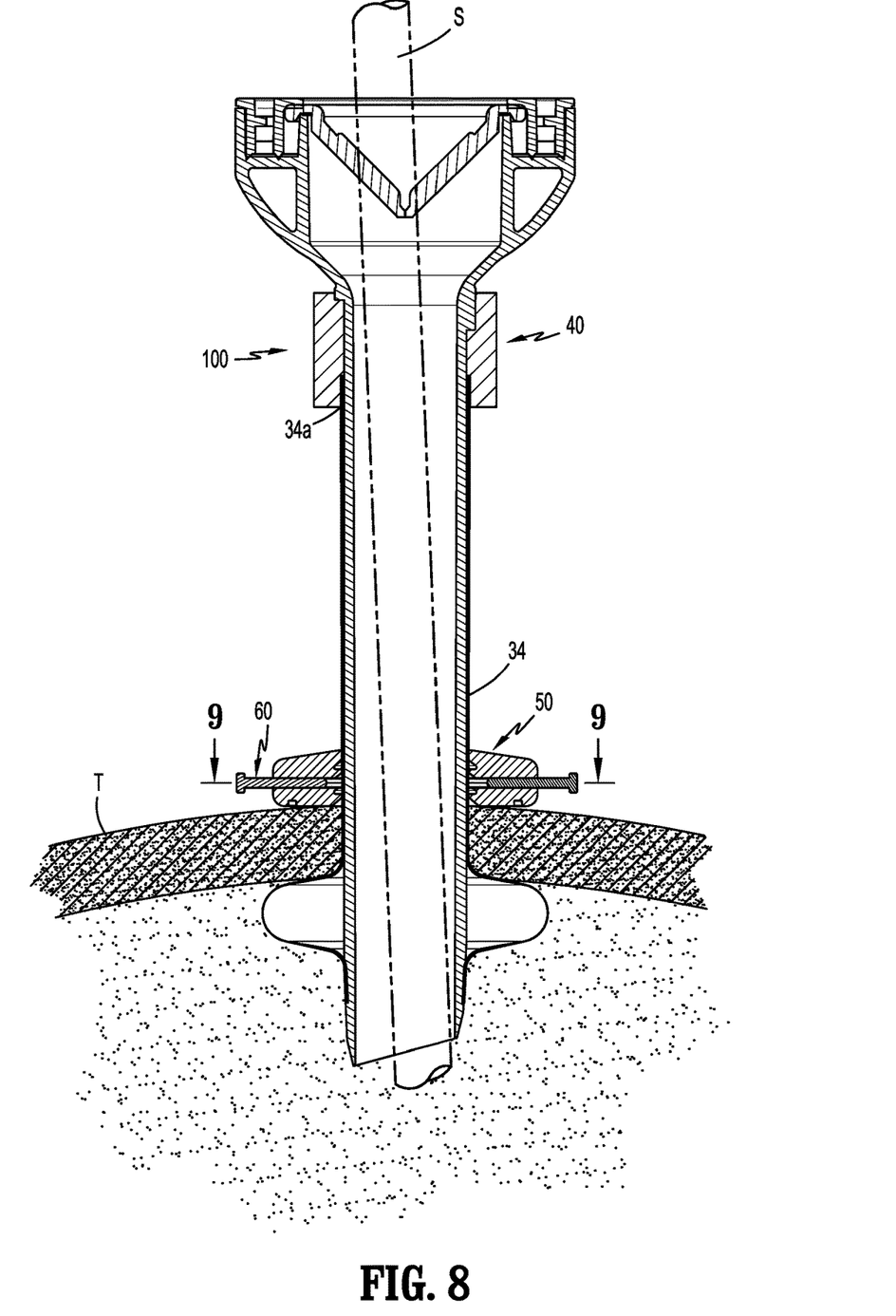
FIG. 8 is a side cross-sectional view of the surgical access device of FIG. 1 positioned in tissue with the balloon anchor in an expanded configuration and the disc in contact with an outer surface of tissue.

With brief reference now to FIG. 4, the balloon anchor 30 includes the expandable portion 32 and a sleeve 34. The sleeve 34 includes the proximal portion 34a that extends proximally and a distal portion 34b that extends distally from the expandable portion 32. The proximal portion 34a may extend into a body of the valve assembly (FIG. 8). The expandable portion 32 is fluidly coupled to the valve assembly 40 such that an inflation fluid may be introduced into the balloon anchor 30 for expanding the expandable portion 32 of the balloon anchor 30. It is contemplated that the inflation fluid may be removed from the expandable portion 32 of the balloon anchor 30 via the valve assembly 40. The expandable portion 32 is transitionable between a collapsed configuration (FIG. 2) and an expanded configuration (FIG. 1) that is also shown in phantom in FIG. 4. The proximal and distal portions 34a, 34b of the sleeve are secured to the outer surface of the cannula tube 20 (see FIG. 8). The proximal and distal portions 34a, 34b are secured using know techniques such as ultrasonic welding, adhesives, etc.

Figure 9:
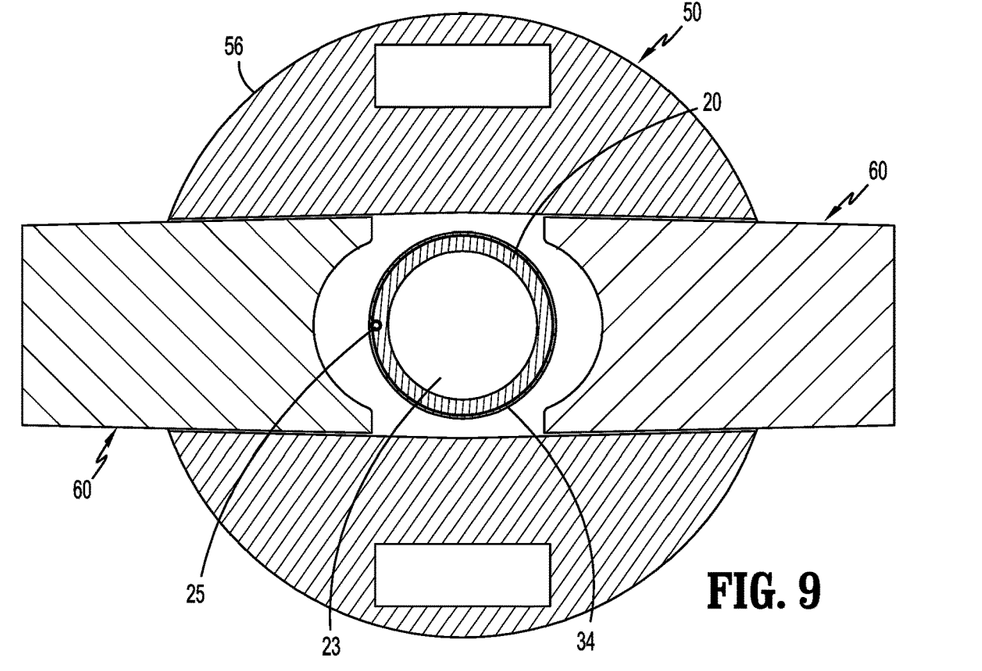
FIG. 9 is a top cross-sectional view of the cannula tube, the proximal portion of the balloon anchor, the disc, and the blades in a retracted position taken along section line 9-9 of FIG. 8.
Figure 10:
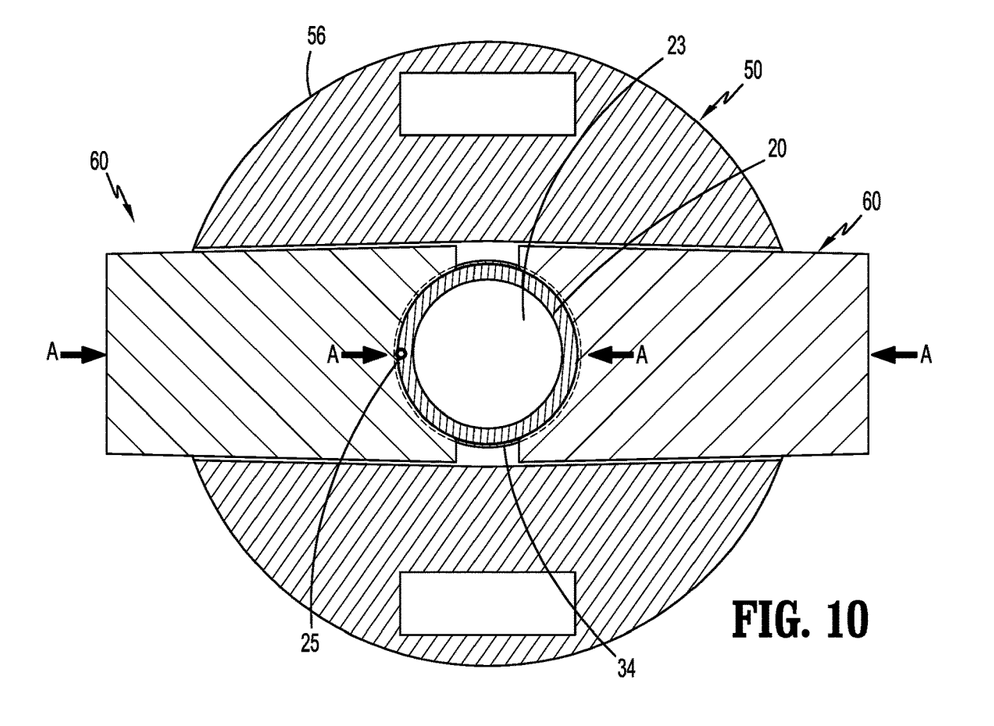
FIG. 10 is a top cross-sectional view of FIG. 9 with the blades in the extended position and in contact with the proximal portion of the balloon anchor.
Figure 11:
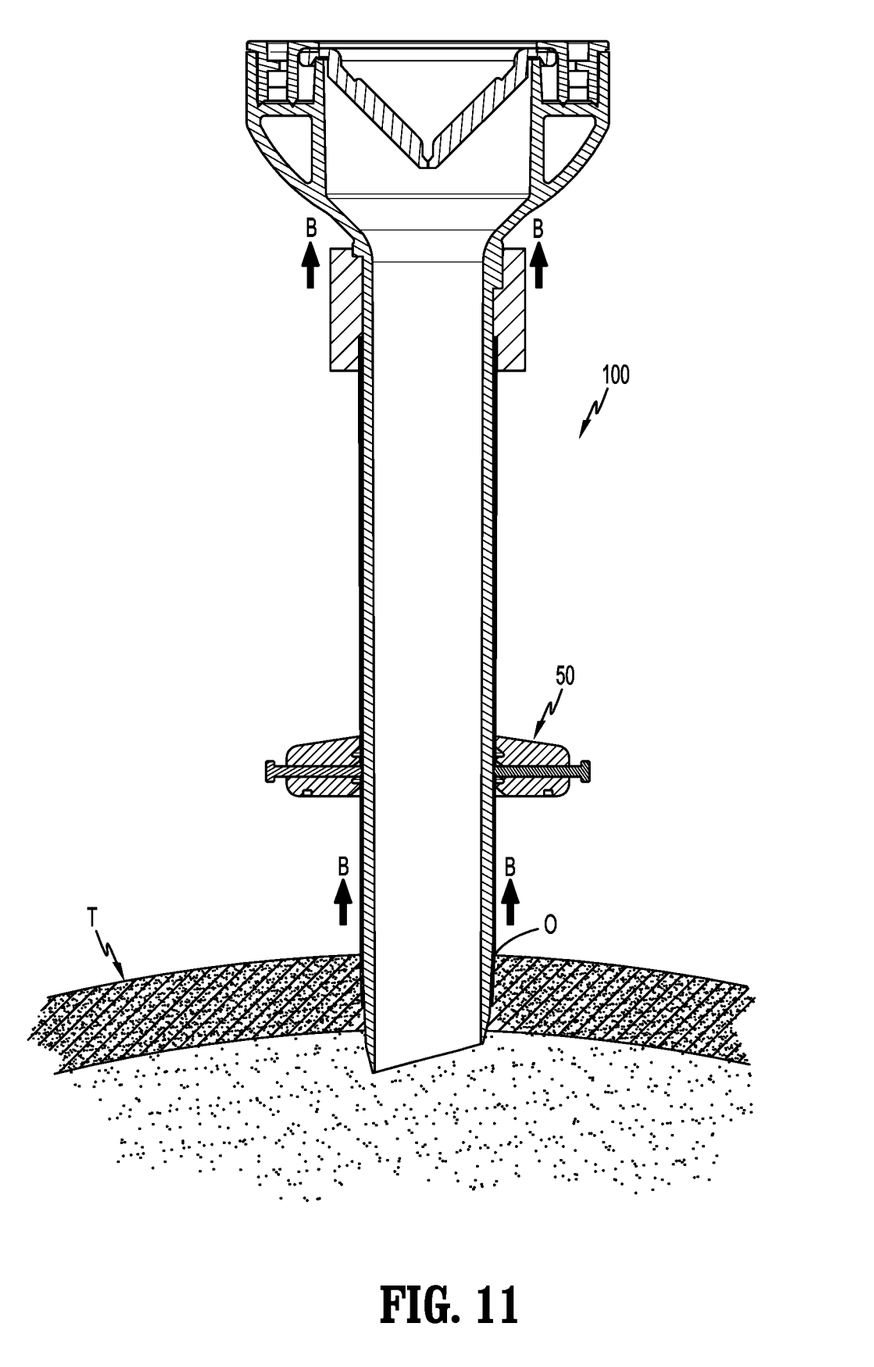
FIG. 11 is a side cross-sectional view of the surgical access device of FIG. 8 with the balloon anchor in the collapsed configuration and the surgical access device partially removed.

The surgical access device 100 is positionable through a patient's tissue "T" to access an underlying surgical site (FIG. 8). Once placed through an opening "O" in the patient's tissue "T", the expandable portion 32 of the balloon anchor 30 is transitioned from the collapsed configuration to the expanded configuration and the disc 50 is slid distally along the outer surface of the cannula tube 20 into contact with an outer surface of the patient's tissue "T" to assist in securing the surgical access device 100 in position. This arrangement allows a clinician to perform a surgical procedure using a surgical instrument "S". As shown in FIG. 9, the first and second blades 60 are in the extended position. Once the clinician is ready to remove the surgical access device 100 from the opening "O" in the patient, the clinician slides one or both blades 60 towards the cannula tube 20 (FIG. 10) in the direction of arrows "A" such that one or both of the knife edges 62 of the blades 60 engages the proximal portion 34a of the sleeve 34 of the balloon anchor 30 and pierces the material. This allows the inflation fluid in the balloon anchor 30 to escape and allows the pressure in the balloon anchor 30 to equalize with the ambient pressure surrounding the surgical access device 100. Once the balloon material is pierced, the expandable portion 32 of the balloon anchor 30 collapses to permit easy withdrawal of the surgical access device 100 (FIG. 11) from the opening "O" in the patient's tissue "T" in the direction of arrows "B".

Persons skilled in the art will understand that the devices and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A surgical access device comprising:
   an elongate tubular member having proximal and distal regions, the elongate tubular member defining a passage therethrough;
   a balloon anchor disposed in the distal region of the elongate tubular member, the balloon anchor including an expandable portion and a first portion, the first portion of the balloon anchor extending proximally from the expandable portion along an outer surface of the elongate tubular member;
   a valve assembly disposed in the proximal region of the elongate tubular member, the valve assembly fluidly coupled to the balloon anchor;
   a disc slidably disposed on the elongate tubular member; and
   a first blade having a first sharpened edge, the first blade slidably disposed in the disc and transitionable between a retracted position and an extended position, the first sharpened edge configured to penetrate the first portion of the balloon anchor at a location longitudinally spaced from the expandable portion.

2. The surgical access device of claim 1 further including a valve housing disposed in the proximal region of the elongate tubular member.

3. The surgical access device of claim 1, wherein the expandable portion of the balloon anchor is transitionable between a collapsed configuration and an expanded configuration.

4. The surgical access device of claim 1, wherein the disc includes a second blade transitionable between a retracted position and an extended position, the second blade having a second sharpened edge.

5. The surgical access device of claim 4, wherein translation of the first and second blades from the retracted positions to the extended positions penetrates the first portion of the balloon anchor.

6. A method of removing a surgical access device from a surgical site comprising:
   sliding a disc distally along an elongate tubular member of a surgical access device;
   moving a blade of the disc towards an outer surface of the surgical access device;
   penetrating a first portion of a balloon anchor with a sharpened edge of the blade such that pressure within an expandable portion of the balloon anchor equalizes with ambient pressure, wherein the first portion of the balloon anchor is longitudinally spaced from the expandable portion of the balloon anchor; and
   removing the surgical access device from the surgical site.

7. The method of claim 6, wherein penetrating the first portion of the balloon anchor includes rotating the disc with the sharpened edge of the blade engaged with the first portion of the balloon anchor.

* * * * *